United States Patent [19]

Sarosiek et al.

[11] Patent Number: 5,730,958
[45] Date of Patent: Mar. 24, 1998

[54] METHOD OF TREATMENT OF GASTROESOPHAGEAL REFLUX DISEASE BY ENHANCEMENT OF SALIVARY ESOPHAGEAL PROTECTION DUE TO MASTICATION

[75] Inventors: Jerzy Sarosiek; Richard McCallum, both of Charlottesville, Va.

[73] Assignee: The University of Virginia Patents Foundation, Charlottesville, Va.

[21] Appl. No.: 697,003

[22] Filed: Aug. 16, 1996

Related U.S. Application Data

[60] Provisional application No. 60/002,511, Aug. 18, 1995.
[51] Int. Cl.$^6$ .............. A61K 9/68; A61K 9/28; A61K 9/14
[52] U.S. Cl. .............. 424/48; 424/441; 424/485
[58] Field of Search .............. 424/48, 441, 485

[56] References Cited

U.S. PATENT DOCUMENTS

| | | | |
|---|---|---|---|
| 5,154,927 | 10/1992 | Song et al. | 424/440 |
| 5,424,084 | 6/1995 | Schmidt et al. | 424/78.37 |
| 5,541,165 | 7/1996 | Turgeon | 514/54 |

*Primary Examiner*—Raymond Henley, III
*Attorney, Agent, or Firm*—Oblon, Spivak, McClelland, Maier & Neustadt, P.C.

[57] ABSTRACT

Prolonged mastication is demonstrated to enhance salivary secretion as well as enhance secretion of salivary components such as salivary bicarbonate, epidermal growth factor, mucin, $PGE_2$ and transforming growth factor$_\alpha$. Mastication beginning prior to about 30 minutes in advance of any meal may reduce sensations of heartburn in patients and has therapeutic value in the treatment of patients with reflux esophagitis and gastroesophageal reflux disease. Post-meal chewing is of additional value in alleviating severe symptoms.

11 Claims, 4 Drawing Sheets

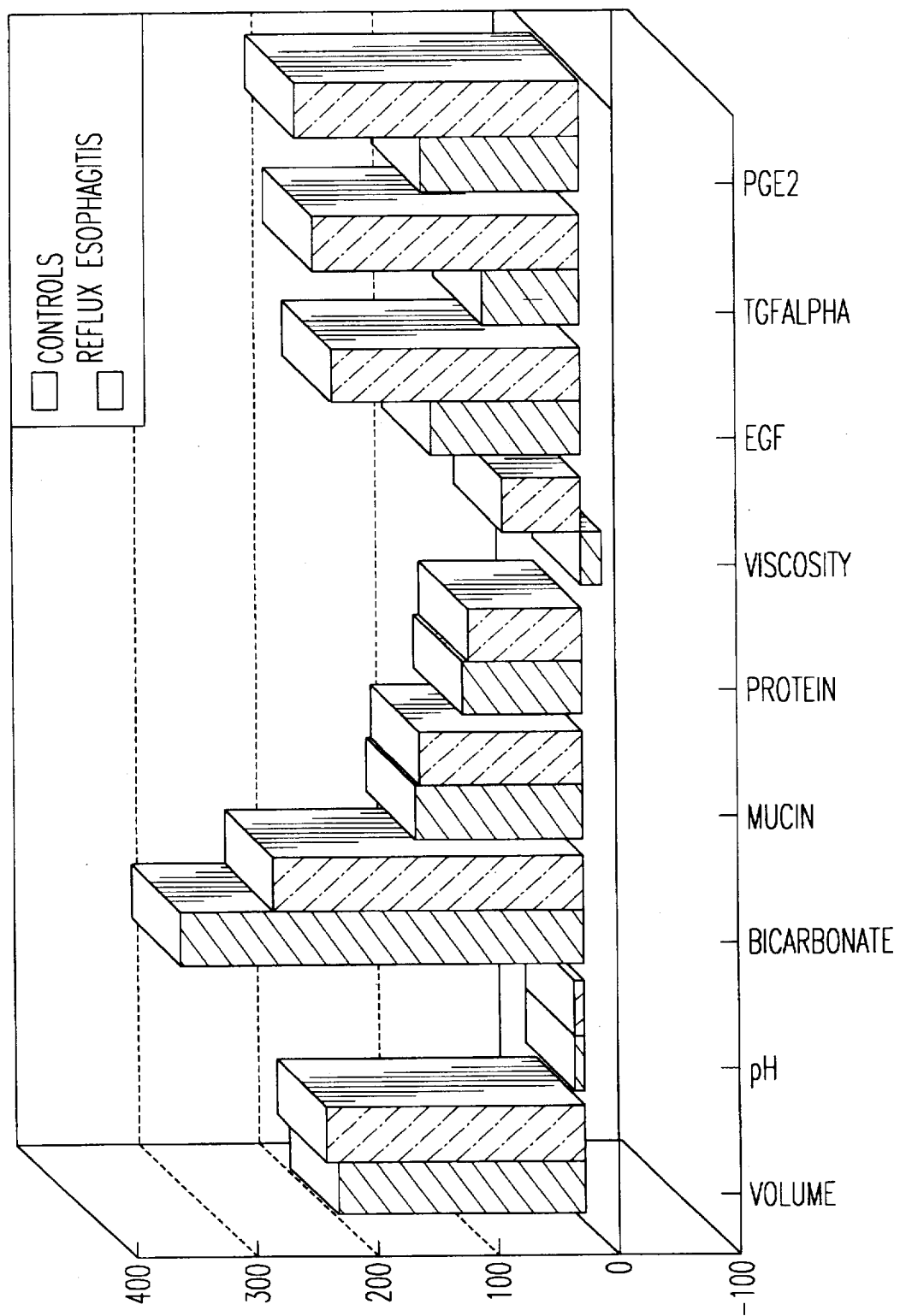

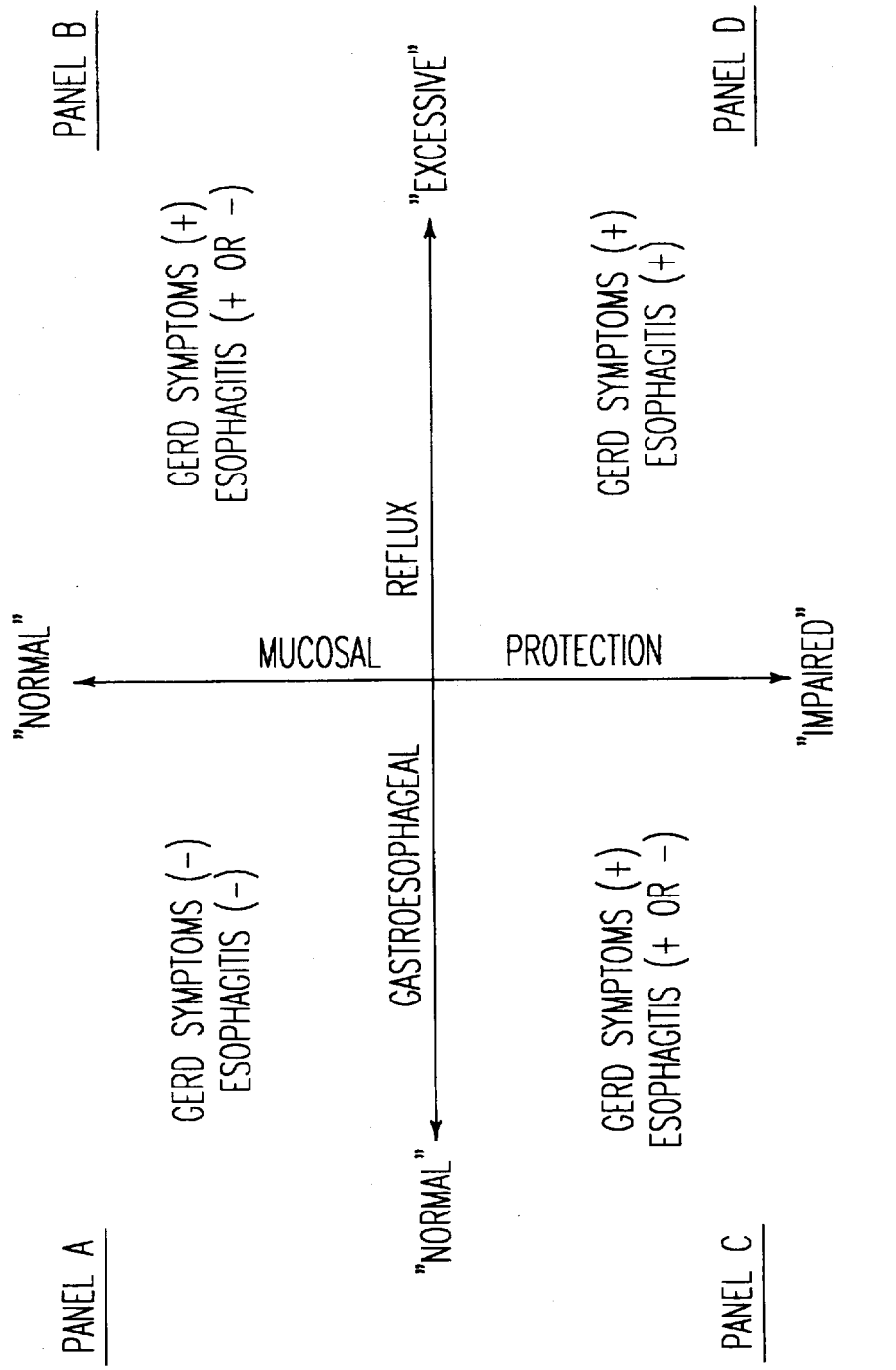

METHOD OF TREATMENT OF GASTROESOPHAGEAL REFLUX DISEASE BY ENHANCEMENT OF SALIVARY ESOPHAGEAL PROTECTION DUE TO MASTICATION

This application claims priority of U.S. Provisional application Ser. 60/002,511, filed Aug. 18, 1995.

BACKGROUND OF THE INVENTION

Field of the Invention

This invention pertains to a method of treating gastroesophageal reflux disease (GERD) by encouraging patients suffering from the same to chew, or masticate. Mastication, both pre- and post-meal chewing, improves esophageal protection, useful in treating and controlling GERD. Those who suffer from endoscopic RE may also benefit from such mastication, as an augment to other available therapies. The item chewed may be any non-toxic chewable item that will support an extended period (at least about 30 minutes) of chewing, including conventional chewing gums, inert plastic films, leather and the like.

BACKGROUND OF THE PRIOR ART

The protective role of salivary inorganic and organic components in the maintenance of the esophageal mucosal integrity both in the experimental and clinical settings is a rapidly evolving research arena. It has been demonstrated experimentally that surgical removal of salivary glands in rats resulted in 108% increase in the rate of permeability of the esophageal mucosa to hydrogen ion accompanied by an 83% decline in the content of mucus within the pre-epithelial mucosal barrier. Sarosiek et al., Am. J. Med. Sci. 302:359-363 (1991). Clinical studies have revealed that salivary buffering capacity is pivotal in restoration of pH within the pre-epithelial barrier as assessed by 24 hour pH monitoring. Helm et al., Gastroenterology 83:69-74(1982). In addition, a plethora of salivary organic components such as epidermal growth factor (EGF), mucin, $PGE_2$ and transforming growth factor$_\alpha$ ($TGF_\alpha$) well known for their protective potential within the oral cavity and gastric mucosa, are shown to have a significant impact on the integrity of the esophageal mucosal barrier. Therefore, a quantitative and qualitative enhancement of salivary secretion that could benefit protective mechanisms operating within the esophageal pre-epithelial barrier, crucial in the combat of gastroesophageal reflux (GER) is an object of these of skill in the art.

We have demonstrated, in a pilot study of controls and patients with reflux esophagitis (RE), when given masticatory stimulus, without any gustatory component, significantly increase salivary volume and pH in controls and significantly enhanced EGF output both in controls and patients with endoscopic RE. Li et al., Am. J. Gastroenterol 88:1749-55 (1993) and Sarosiek et al., Am. J. Med. Sci. 302:359-363 (1991). If masticatory stimulation leads also to a significant enhancement of the rate of secretion of other salivary inorganic and organic protective components, mastication could potentially become one of the most physiologic modalities in the treatment of GERD and endoscopic RE. However, the rate of secretion of salivary bicarbonate, $TGF\alpha$, $PGE_2$, mucin, protein, viscosity and pH of saliva in patients with endoscopic RE under the impact of masticatory stimulation remains unknown.

SUMMARY OF INVENTION

Accordingly, we provide, evidence for the first time in humans, that masticatory stimulation has a profound and significant impact on salivary bicarbonate, $PGE_2$, mucin, and protein in humans and is of a value as a new treatment regimen. In addition, we provide further data based on larger studied groups, supporting our findings from the previous pilot study Roark et al., Am. J. Gastroenterol. 89:237-244 (1994) that mastication exerts a significant impact on salivary volume, pH and EGF in both controls and patients with endoscopic RE. Thus, pre- and post-meal chewing for extended periods is effective in the treatment and control of GERD.

BRIEF DESCRIPTION OF THE DRAWINGS

These objects, and others, are made more clear by reference to the following disclosure and figures.

Figures

FIG. 3. Percent change in salivary parameters during mastication in controls and patients with reflux esophagitis.

FIG. 4. Pathogenesis of symptomatic GERD and endoscopic reflux esophagitis.

DETAILED DESCRIPTION OF THE INVENTION

Subjects & Methods

Subjects

Figure 1:
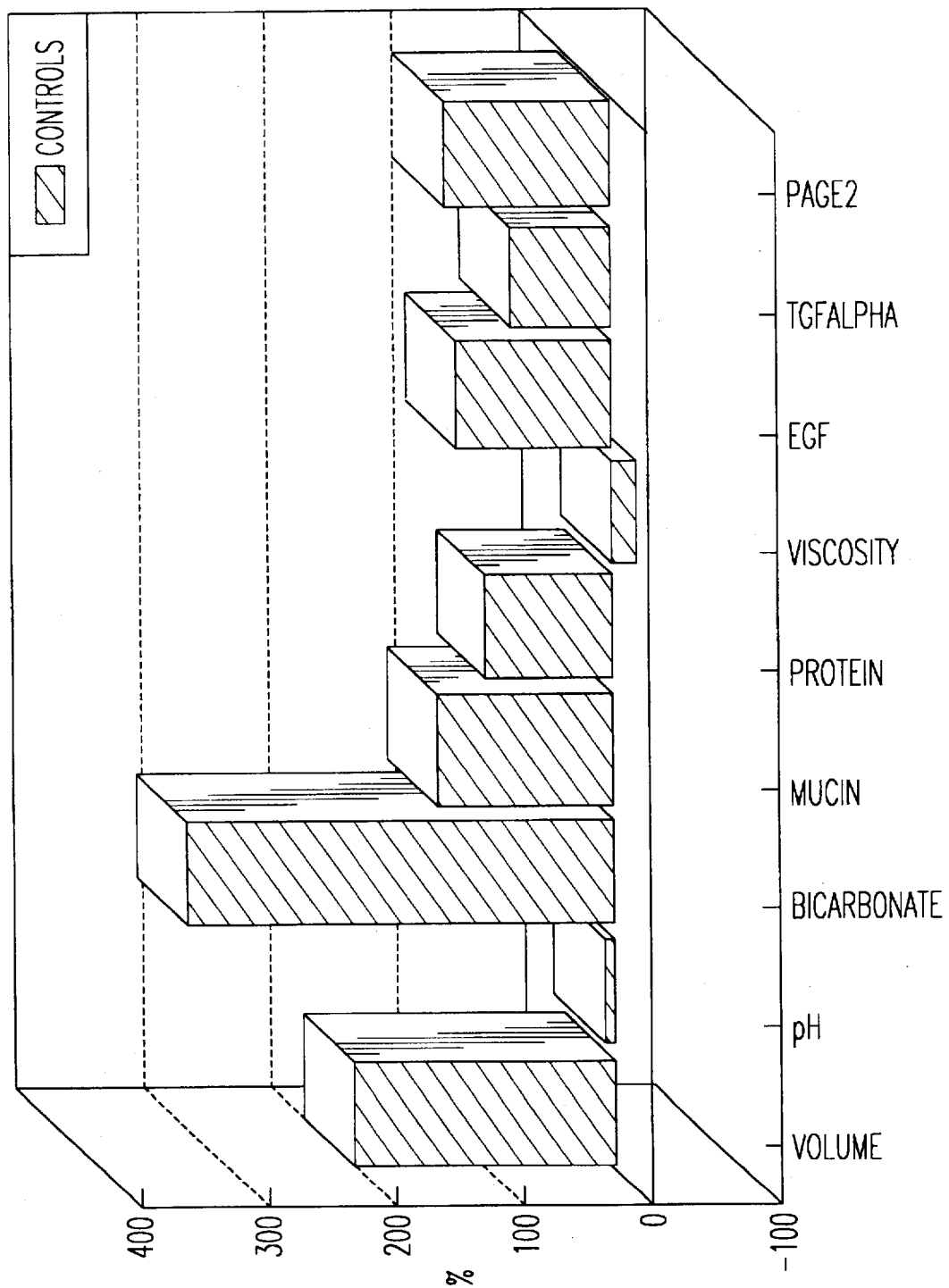
FIG. 1. Percent change in salivary parameters during mastication in controls.

All studies were approved by the Human Investigation Committee at the University of Virginia Health Sciences Center (Protocol number 5140). Consent was obtained from all subjects.

Thirty six patients with RE (13 females and 23 males; mean age 47; range 24-79) and 31 asymptomatic volunteers (12 females and 19 males; mean age of 42; range 22-65) were studied (Table I). RE group was graded endoscopically including 16 grade II, 6 Grade III, 10 Grade III with Barrett's, 4 Grade III with Stricture. All medication was discontinued for 72 hours before the collection procedure.

Methods

Salivary volume, in samples collected on ice as described previously (2,3,5), was assessed using a sialometer (Proflow Incorporated, Amityville, N.Y.).

Salivary pH was monitored using Expandable Ion Analyzer EA 940 (Orion Res., Boston, Mass.).

Salivary bicarbonate was measured by titration and back-titration methodology using TitraLab 90 (Radiometer America Inc., Chicago, Ill.) according to Izutsu (12). Saliva forms in the mouth thin film on oral tissues (and similar on the esophagal mucosa) and this allows the evolution of $CO_2$ formed from acid-base interactions. Therefore, the salivary bicarbonate buffer value in the mouth would be that for the open system equilibrated with the $CO_2$ tension of the mouth (approx. 20 mmHg)(12). This was the rationale for choosing titration (from starting pH to pH of 4.0 for assessment of salivary bicarbonate in an open system (without covering with a layer of liquid paraffin oil) with continuous $CO_2$-free bubbling. The difference in the amount of acid initially required to titrate the sample from its staring pH to pH 4.0 and the amount of base required to back-titrate the sample to its original pH after evolution of the $CO_2$ was used to calculate the bicarbonate concentration of the sample (12). In addition, this method was validated by titration of the known concentration of bicarbonate in the standard solutions.

Salivary viscosity was recorded with a Cone/Plate Digital Viscometer (1.565 cone) equipped with DV Gather software for IBM PC (Brookfield, Stockton, Mass.) as described previously (4).

Salivary mucin was measured using periodic acid Schiff (PAS) methodology as described before (13,14). Solutions of human salivary mucin (5–50 μg/ml) purified by density gradient ultracentrifugation in CsCl were used for a standard curve (13).

Salivary EGF was assessed by RIA using a commercially available kit (Amersham, Arlington Heights, Ill.) as it has been described in our previous publications (2,3,15,16).

Salivary TGFα was recorded using commercially available RIA kit (Biomedical Technologies Inc.; BTI, Stoughton, Mass.) as we described recently (17). This assay is based on highly specific sheep anti-human TGFα antibodies which have been shown to lack significant cross-reactivity with a large excess of structurally related growth factors. The separation between bound and unbound EGF was performed using a donkey anti-sheep IgG and PEG. In the final calculations of EGF concentrations, nonspecific binding was always considered. Human recombinant TGFα (BTI) was used for a standard curve. All samples were centrifuged at 4° C. and 3000 rpm (2500 g) for 20 min, which are conditions required to spin down cellular debris, plasma membrane sheets and nuclei.

Salivary $PGE_2$ was measured using RIA kit (Amersham, Arlington Heights, Mass.) as outlined in our previous publication (18). This RIA method is based on highly specific antibodies directed to oximated form of $PGE_2$ (18).

Salivary protein was monitored by Lowry methodology as described previously (13).

Statistical analysis was performed using Σ-Stat software for IBM PC (Jandel Sci., San Rafael, Calif.). Results are presented as a mean ±SEM.

RESULTS

The basal rate of salivation in controls was 0.59±0.06 ml/min and significantly increased to 1.53±0.13 ml/min while chewing parafilm (P<0.0001)(Table II). This also significantly enhanced the salivary pH (6.77±0.07 to 7.28±0.08; P<0.0001) and bicarbonate output (1.78±0.28 μEq/min to 6.71±1.75 μEq/min; P=0.002). Chewing parafilm significantly enhanced the content of salivary mucin (0.58±0.08 mg/min to 1.15±0.16 mg/min; P<0.0001), and protein (2.83±0.48 mg/min to 4.07±0.49 mg/min; P<0.0001). Viscosity of basal saliva in controls was 33.2±5.82 centipoises and declined to 19.6±2.54 centipoises (P=0.085) during parafilm chewing. The rate of salivary EGF secretion was significantly enhanced by mastication (1.89±0.29 ng/min to 5.01±1.18 ng/min; P=0.031) and TGFα secretion showed an increasing trend (82.7±36.6 pg/min to 122±58.7 pg/min; P>0.100) while chewing parafilm. Salivary $PGE_2$ output in basal saliva was 124±38.2 pg/min and significantly increased to 211±45.7 pg/min (P<0.0001) during chewing. Thus the rate of salivary volume, pH, bicarbonate, mucin, protein, EGF, TGFα, $PGE_2$ increased during mastication by 205±36.7%, 7.6±0.86%, 335±84.8% 137±26.3%, 98±23.0%, 123±30.4%, 80±47.6%, 132±21.2% respectively, whereas viscosity declined 19.2±8.2% as compared with corresponding basal values (FIG. 1).

Figure 2:
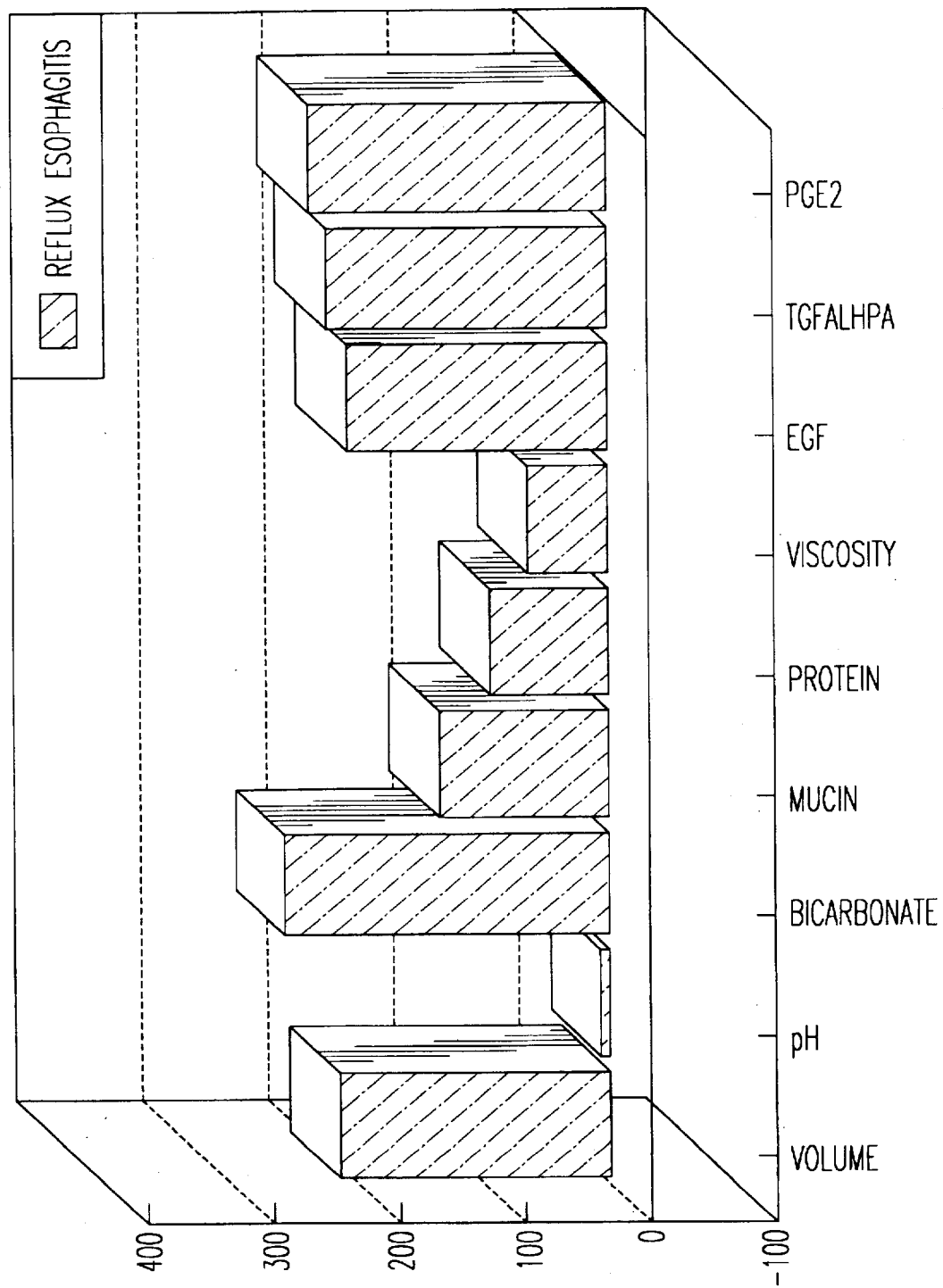
FIG. 2. Percent change in salivary parameters during mastication in patients with reflux esophagitis.

Results recorded in patients with RE were as follows (Table II): the basal rate of salivary secretion was 0.59±0.07 ml/min and significantly increased during masticatory stimulation of salivary glands to 1.37±0.13 ml/min (P<0.0001). Chewing the parafilm also significantly enhanced salivary pH (6.94±0.06 to 7.37±0.06; P<0.0001) and the rate of bicarbonate secretion (2.47±0.28 μEq/min to 9.64±3.03 μEq/min; P=0.0001. Chewing parafilm significantly enhanced the content of salivary mucin (0.63±0.08 mg/min to 1.24±0.26 mg/min; P<0.0001) and protein (2.12±0.16 mg/min to 3.58±0.30 mg/min; P<0.0001). Viscosity of basal saliva in RE was 93.8±26.6 centipoises and decreased to 60.8±17.7 centipoises (P>0.100) during parafilm chewing. The secretion rate of salivary EGF was significantly enhanced by chewing (1.27±0.20 ng/min to 2.40±0.45 ng/min; P<0.0001) and, again, TGFα secretion showed an increasing trend (38.3±12.1 pg/min to 109±44.3 pg/min; P>0.100). Salivary $PGE_2$ output in basal saliva was 86.7±18.4 pg/min and significantly increased to 243±65.3 pg/min (P<0.0001). Mastication resulted in an increase in salivary volume, pH, bicarbonate, mucin, protein, viscosity, EGF, TGFα, and $PGE_2$ by 215±39.0%, 6.8±0.69%, 257±70.4%, 135±34.5%, 94.4±22.9%, 64.3±53.4%, 207±125%, 225±191%, 240±75.1% respectively (FIG. 2).

Although patients with RE exhibited a general tendency to smaller secretory response in terms of bicarbonate during masticatory stimulation, the rate of secretion of EGF, TGFα and $PGE_2$ exhibited tendencies to higher values (FIG. 3). All differences between RE and controls populations were not statistically significant.

DISCUSSION

Evidence is accumulating that GERD, especially accompanied by endoscopic RE, results from a disequilibrium between excessive mucosal exposure to aggressive factors, predominantly acid and pepsin, and impaired esophageal defense mechanisms, particularly those within the pre-epithelial barrier. Li et al., supra; Namiot et al., Gastroenterolgy 106:973–981 (1994) and Sarosiek et al., Am. Jur. Gastroenterol 89:588–594 (1994) among others. An impairment in the rate of secretion of salivary EGF, esophageal EGF and esophageal mucin in patients with endoscopic RE has been demonstrated. In addition, diminished esophago-salivary reflex-mediated salivary secretory response in terms of its buffering capacity in endoscopic RE has also been revealed. Sarosiek et al., J. Pract. Gastroenterol. 18:205–209 (1994) Therefore, a therapeutic strategy that enhances salivary secretion and its protective components may be used to balance aggressive factors and is clinically relevant.

By application of sasticatory stimulation with a tasteless parafilm we demonstrated a significant quantitative and qualitative enhancement of salivary secretion in demographically similar populations of controls and RE. In asymptomatic volunteers, a 3-fold increase in salivary volume, 4-fold increase in bicarbonate, approximately 2-fold enhancement in mucin, protein, EGF, TGFα, and $PGE_2$, without major changes in viscosity were observed. Similar findings were seen in patients with endoscopic RE though the increases in EGF, TGFα and $PGE_2$ were even more dramatic with a rising trend in viscosity. Therefore, masticatory stimulation seems to be equally effective in stimulation of salivary protective components in both populations studied, and it seems reasonable to assume that patients with GERD, with and without endoscopic RE, could potentially benefit from the application of masticatory stimulation for the treatment of GER related mucosal pathology and resulting symptoms.

All of these investigated parameters are well known for their protective potential within the alimentary tract mucosa. Salivary volume dilutes intraluminal acid and pepsin without gastroesophageal refluxate. Its acid clearing capacity, related to the content of bicarbonate and non-bicarbonate buffers directly corresponding to its pH, have a profound impact on regional esophageal distribution and clearance of acid from GER.

Salivary and esophageal mucins are the major components of the mucus-bicarbonate barrier, which has been demonstrated recently within the esophagus. Sarosiek et al., The Esophageal Mucosa, 278–290 (1994 Elsevier). The protective role of mucin depends not only upon its ability to provide an architectural framework for the unstirred layer of the mucus-bicarbonate barrier, but also on its ability to retard hydrogen ion diffusion through hydrophobicity and interaction with phospholipids. Mucus-bicarbonate layer maintains a pH gradient between the luminal and apical values of 3.29±0.32 and 4.48±0.15 respectively; P<0.02. This gradient, though smaller than that overlying the mucosa of the body of the stomach, is similar to the pH gradient value recorded in the antrum and higher than that of the duodenal mucosa.

EGF is also protective within the oral, esophageal and gastric mucosa not only preventing the damage to the surface epithelium but promoting restitution and restoration of the integrity of the alimentary tract mucosa. The protective characteristics of TGFα have been recently demonstrated within the gastric mucosa as well. Polk et al., Gastroenterology 102:1467–1474 (1992). TGFα mediated protection against aspirin-induced mucosal damage is accompanied by a dose-dependent increase in the content of gastric mucin. Increased production of TGFα following acute gastric injury with HCl strongly suggests that its local production after injury may play a significant role in mucosal restitution and repair after injury. The EGF receptor, which binds EGF and TGFα, has been recently demonstrated on the luminal aspect of the esophageal surface epithelium. Janowski et al., Gut 33:439–443 (1992).

$PGE_2$ is well known for its protective potential against various thermal and chemical insults when topically applied to the gastric mucosa. This protective potential of prostaglandin resulted in the development of its clinical formulas, currently used as a preventive measure in patients with a high risk for the development of gastric injury after chronic administration of nonsteroidal anti-inflammatory agents. While the full role of $PGE_2$ in the balance between aggressive factors and protective mechanisms within the esophageal mucosal compartment still remains to be elucidated, there is a growing evidence that this molecule exerts a protective impact. Since $PGE_2$ has an ability to enhance the physical properties of the mucus layer, especially its ability to retard hydrogen ion diffusion, its use in the pre-epithelial defense against GER may be of value to afflicted patents.

Viscosity of alimentary tract secretions is a multidimensional parameter which seems to have an important role in mucosal protection. A unique composition and structure of mucin allows it to interact with various molecules such as phospholipids, $PGE_2$, albumin, immunoglobulins resulting in generation of viscous and permselective barrier to hydrogen ion on the surface of the gastric mucosa. However, the clinical impact of salivary viscosity on the esophageal pre-epithelial defense is unclear at the present time. Our data showed no change in salivary viscosity after mastication in asymptomatic volunteers but an increasing trend in patients with RE patients. A lower viscosity of Salivary secretion may relieve GERD symptoms more effectively due to rapid transit along the esophagus after each swallow and under the impact of gravity. This may result in an accelerated delivery of bicarbonate to the lower segment of the esophageal mucosa where exposure to acid/pepsin lasts for the longest period of time. On the other hand, more viscous, tenacious saliva may Be more adherent to the surface of the esophageal mucosa and better preserve the thickness of the mucus layer, providing a stronger mucus-bicarbonate barrier to luminal aggressive factors, predominantly acid and pepsin.

Of note, the rate of secretion of esophageal protective components such as mucin, EGF, $PGE_2$, TGFα and protein significantly declined during the mucosal exposure to pH below 2.0. Therefore, an enhancement of salivary secretion achieved by any means may play a significant compensatory role within the pre-epithelial barrier and help to restore an equilibrium between aggressive factors and protective mechanisms.

There are several groups of compounds which appeared to be useful in the medical therapy of GERD and endoscopic RE. These include prokinetic agents, agents enhancing the pre-epithelial and epithelial barriers and drugs suppressing gastric acid. In severe cases, the effective treatment of endoscopic RE, however, requires a high dose of acid suppressing agents, and dose reduction for maintenance therapy frequently results in relapse of endoscopic changes. Long-term acid suppressive therapy, though considered safe, may result in bacterial overgrowth and secondary hypergastrinemia. Therefore, as masticatory stimulation of salivary flow results in a reduction of prokinetic or acid suppressing drug doses, it may be able to provide a significant clinical and economic benefit.

Based on the results of our studies the GERD and endoscopic RE result from a pathogenetic interplay between the aggressive factors represented by gastroesophageal reflux (GER) and protective mechanisms embodying mucosal defense (FIG. 4). When both the extent of GER and mucosal protection are normal, heartburn and endoscopic changes should not develop (Panel A). When mucosal protection is selectively impaired with only the usual amount of GER, heartburn symptomatology without endoscopic changes may result (Panel B). A similar clinical outcome will develop with excessive GER and intact mucosal defense (Panel C). However, when excessive GER is accompanied by impaired mucosal protection, moderate to severe endoscopic RE with relevant symptomatology would inevitably develop (Panel D). The extent of GER and quality of protection are highly dynamic phenomena which may lead to cyclic exacerbations and cessations of symptomatology and endoscopic changes.

Masticatory stimulation of salivary secretion results in a significant increase in salivary volume, pH, bicarbonate, mucin, protein, EGF and $PGE_2$, accompanied by a moderate increase in TGFα in both controls and patients with endoscopic RE. Our data demonstrates that, by application of masticatory stimuli, i.e., inducing, chewing, we are able to significantly enhance mucosal protection and potentially could restore an equilibrium between aggressive factors and protective mechanisms within the esophageal pre-epithelial barrier.

The profound and significant increase in the rate of secretion of inorganic and organic component in saliva during masticatory stimulation suggests its potential value as a therapeutic agent in the treatment of patients with GERD not accompanied by endoscopic RE or as adjunct therapy in mild, moderate to severe endoscopic RE. In patients with endoscopic RE, the effect of pre-and-post-meal chewing may simply be to reduce the level of medication required to treat the condition.

Depending on the degree and intensity of symptoms experienced, generically referred to as "heartburn", mastication should begin about 30 minutes in advance of any meal. More severe conditions may require a longer period of chewing than 30 minutes. Some patients may require as much as 2 hours of chewing immediately prior to any meal. Symptoms may also be alleviated some degree by post-meal chewing, particularly in those suffering from severe symptoms. Again, the times necessary for each patient will differ, on an empirical basis, but in general, a post-meal chewing period of about 30 minutes is of value. Post-chewing of about hour or more may additionally help to ease symptoms. The substance chewed may be conventional chewing gum, sugar-free chewing gum, or any other type of gum. The materials selected should be selected so as to provide comfort while chewing, the content is not a pre-requisite for achieving the goals of the invention. In general, sweet substances should be avoided, because of the deleterious impact of sugar, per se. In addition to gums, plastic films, leather thongs and strips, etc. may be equally suitable for chewing. This preference largely lies with the patient.

This invention has been described generically, and with respect to specific conditions in individuals. Variations will occur to those of ordinary skill in the art, particularly in terms of the time or period of chewing, and the substance chewed, without the exercise of inventive faculty. Such variations and modifications remain within the scope of the claims set forth below, unless delimited by the recitations thereof.

Table I

Study Population

| | Asymptomatic Volunteers | Reflux Esophagitis |
|---|---|---|
| Number | 31 | 36 |
| Females/Males | 12/19 | 13/23 |
| Mean Age in Years (Range) | 42(22–65) | 47(23–79) |
| Grades: II | — | 16 |
| III | — | 6 |
| III & BE | — | 10 |
| III & Structure | — | 4 |

What is claimed is:

1. A method for treatment and/or control of gastroesophageal reflux disease (GERD), comprising:

increasing at least one of salivary volume, salivary pH and secretion of an organic agent selected from the group consisting of salivary bicarbonate, prostaglandin $E_2$, TGF-$\alpha$, mucin and epidermal growth factor in a patient suffering from GERD, comprising having said patient who suffers from GERD chew continuously for a period of at least 30 minutes in advance of any meal.

2. The method of claim 1, wherein said patient is caused to chew for a period of at least about 1 hour in advance of any meal.

3. The method of claim 1, wherein said patient is caused to chew for a period of at least about 2 hours in advance of any meal.

4. The method of claim 1, wherein said patient is caused to chew after consuming any meal for a period of at least 30 minutes.

5. The method of claim 4, wherein said patient is caused to chew for a period of at least about 1 hour after every meal.

6. The method of claim 5, wherein said patient is caused to chew for a period of at least about 2 hours after every meal.

7. A method of supporting therapy and treatment of individuals with endoscopic reflux esophagitis, comprising increasing at least one of salivary volume, salivary pH and the secretion of an organic active agent selected from the group consisting of salivary bicarbonate, prostaglandin $E_2$, TGF-$\alpha$, mucin and epidermal growth factor in said individuals, comprising causing a human patient suffering from endoscopic reflux esophagitis to chew for a period of at least about 30 minutes in advance of every meal.

8. The method of claim 7, wherein said patient is caused to chew for a period of at least 30 minutes after consuming every meal.

9. The method of claim 1, wherein said patient is caused to chew a substance which is selected from the group consisting of sugar-free chewing gum, non-sugar-free chewing gum, plastic film, leather and combinations thereof.

TABLE II

Changes in Salivary Parameters at Baseline and After Chewing Parafilm in Asymptomatic Volunteers and Patients with Reflux Esophagitis

| Salivary Parameter | Asymptomatic Volunteers | | | Reflux Esophagitis | | |
|---|---|---|---|---|---|---|
| | Basal | Parafilm | P | Basal | Parafilm | P |
| Volume (ml/min) | 0.59 ± 0.06 | 1.53 ± 0.13 | P < 0.0001 | 0.59 ± 0.07 | 1.37 ± 0.13 | P < 0.0001 |
| pH (units) | 6.77 ± 0.07 | 7.28 ± 0.08 | P < 0.0001 | 6.94 ± 0.06 | 7.37 ± 0.06 | P < 0.0001 |
| $HCO_3^-$ (μEq/min) | 1.78 ± 0.28 | 6.71 ± 1.75 | P = 0.002 | 2.47 ± 0.28 | 9.64 ± 3.03 | P = 0.0001 |
| Mucin (mg/min) | 0.58 ± 0.08 | 1.15 ± 0.16 | P < 0.0001 | 0.63 ± 0.08 | 1.24 ± 0.26 | P < 0.0001 |
| Protein (mg/min) | 2.83 ± 0.48 | 4.07 ± 0.49 | P < 0.0001 | 2.12 ± 0.16 | 3.58 ± 0.30 | P < 0.0001 |
| Viscosity (units) | 33.2 ± 5.82 | 19.6 ± 2.54 | P = 0.085 | 93.8 ± 26.6 | 60.8 ± 17.7 | P > 0.100 |
| EGF (ng/min) | 1.89 ± 0.29 | 5.01 ± 0.18 | P = 0.031 | 1.27 ± 0.20 | 2.40 ± 0.45 | P < 0.0001 |
| TGF-$\alpha$ (pg/min) | 82.7 ± 36.6 | 122 ± 58.7 | P > 0.100 | 38.3 ± 12.1 | 109 ± 44.3 | P > 0.100 |
| $PGE_2$ (pg/min) | 124 ± 38.2 | 211 ± 45.7 | P < 0.0001 | 86.7 ± 18.4 | 243 ± 65.3 | P < 0.0001 |

10. The method of claim 7, wherein said patient is caused to chew a material selected from the group consisting of sugar-free chewing gum, non-sugar-free chewing gum, plastic film, leather and combinations thereof.

11. A method of increasing at least one of salivary volume, salivary pH, and the secretion of an organic active agent selected from the group consisting of salivary bicarbonate, prostaglandin $E_2$, TGF-$\alpha$, mucin and epidermal growth factor in a patient suffering from GERD, comprising inducing said patient to chew for a period of at least about 30 minutes, continuously.

* * * * *